United States Patent [19]

Meissner et al.

[11] 4,192,820

[45] Mar. 11, 1980

[54] PREPARATION OF 3-METHYL-2-BUTEN-1-AL

[75] Inventors: Bernd Meissner, Heidelberg; Werner Fliege, Otterstadt; Otto Woerz, Ludwigshafen; Christian Dudeck, Limburgerhof; Hans Diehm, Mannheim, all of Fed. Rep. of Germany

[73] Assignee: BASF Aktiengesellschaft, Fed. Rep. of Germany

[21] Appl. No.: 891,016

[22] Filed: Mar. 28, 1978

[30] Foreign Application Priority Data

Apr. 5, 1977 [DE] Fed. Rep. of Germany ....... 2715208

[51] Int. Cl.² ............................................. C07C 47/02
[52] U.S. Cl. ................................................ 260/601 R
[58] Field of Search .................................. 260/601 R

[56] References Cited

U.S. PATENT DOCUMENTS

| 2,815,383 | 12/1957 | Booth et al. ............ 260/601 R |
| 3,963,783 | 6/1976 | Buchi et al. ............ 260/601 R |
| 4,087,472 | 5/1978 | Hughes .................. 260/601 R |

FOREIGN PATENT DOCUMENTS 2358355  2/1976  Fed. Rep. of Germany ........... 260/601

OTHER PUBLICATIONS

Houben–Weyl, "Methoden der Organischem Chemie," vol. 7/1, pp. 395–396.

*Primary Examiner*—Werren B. Lone
*Attorney, Agent, or Firm*—Keil & Witherspoon

[57] ABSTRACT

3-Methyl-2-buten-1-al is prepared by isomerizing 3-methyl-3-buten-1-al in the presence of acidic or basic compounds. The product is a starting material for the manufacture of dyes, pesticides, pharmaceuticals, plastics and scents.

10 Claims, No Drawings

PREPARATION OF 3-METHYL-2-BUTEN-1-AL

The present invention relates to a novel process for the preparation of 3-methyl-2-buten-1-al by isomerizing 3-methyl-3-buten-1-al in the presence of acidic or basic compounds.

On the subject of the rearrangement of double bonds in unsaturated aldehydes, Houben-Weyl, Methoden der Organischen Chemie, volume 7/1 pages, 395 and 396, states that it appears as if isolated double bonds tend to migrate into the α, β-position relative to the aldehyde group, and records that such isomerizations are in particular initiated by alkali metal alcoholates, aluminum ethylate and pyridine in the presence of copper compounds. Such agents cause aldehydes to undergo an aldol condensation and Houben-Weyl points out that only in a few cases, where the aldol condensation is difficult and at the same time the migration of the double bond is favored, can an isomerization be carried out.

Houben-Weyl (loc, cit., page 384) also discloses that in the case of α, β-unsaturated aldehydes, specifically acrolein and crotonaldehyde, resinification easily occurs in the presence of alkalis. Further, it is known that these aldehydes form, with aliphatic alcohols in the presence of acids or alkalis, saturated β-alkoxyaldehydes and β-alkoxyacetals, α-β-unsaturated acetals or mixtures of these components.

Crotonaldehyde cyclizes in the presence of bases to give dihydro-o-tolylaldehyde and, due to interaction with further crotonaldehyde molecules, to give condensates of higher molecular weight; furthermore, the interaction with the water elminated also results in aldoxanes. Similarly, 3-methyl-2-buten-1-al cyclizes to give 1,1,5-trimethyl-2-formyl-2,4-cyclohexadiene. Equally, the action of heat alone on 3-methyl-2-buten-1-al causes cyclization to give 2-formyl-2,3-dihydro-3,3,4,4-tetramethylpyran; hydroquinone must be added to the end product to prevent chain polymerization (Houben-Weyl, loc. cit., pages 129-131). In the presence of aqueous hydrochloric acid or sulfuric acid, crotonaldehyde gives the dimer and trimer, as well as octatrienal.

We have found that 3-methyl-2-buten-1-al is obtained in an advantageous manner by isomerization of an unsaturated compound, if 3-methyl-3-buten-1-al is isomerized in the presence of a strong acid or of a basic compound at from 50° to 250° C.

The reaction can be represented by the following equation:

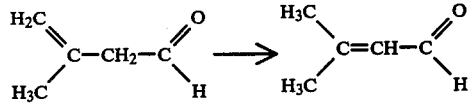

Compared to the prior art, the process according to the invention gives 3-methyl-2-buten-1-al in high yield, high space-time yield and great purity. All these advantageous results are surprising since, in view of the conventional processes, resinification, chain polymerizations, condensation reactions, cyclization of the end product and of the starting materials, and the formation of heterogeneous mixtures containing numerous by-products, would have been expected.

The reaction is carried out at from 50° to 250° C., advantageously from 72° to 225° C., preferably from 120° to 225° C., and especially from 130° to 220° C., under atmospheric or superatmospheric pressure, continuously or batchwise. The residence time in the isomerization chamber is, in continuous or batchwise operation, from 10 seconds to 300 minutes, preferably from 1 to 5 minutes. The isomerization can be carried out in the presence or absence of additional solvents. Preferably, the starting material is used in the form of the reaction mixture from its method of preparation, for example by dehydrogenation of 3-methyl-3-buten-1-ol, especially in accordance with the method described in German Patent Application No. P 27 15 209.6; the following components of such reaction mixtures, the proportion of which may or may not be increased by adding further amounts before starting the reaction, may be used as the above solvent; water, 3-methyl-3-buten-1-ol, 3-methyl-2-buten-1-ol and 3-methylbutan-1-al. Water can advantageously be used in an amount of from 0 to 50, preferably from 2 to 25, percent by weight, based on 3-methyl-3-buten-1-al, whilst the organic solvents may be used individually in an amount of from 0 to 50, preferably from 2 to 40, percent by weight, based on 3-methyl-3-buten-1-al, and the total solvent mixture may be used in an amount of from 0 to 80, preferably from 2 to 50, percent by weight based on 3-methyl-3-buten-1-al. The isomerization may be carried out in a one-phase or two-phase system.

Suitable isomerization catalysts are strong acids or basic compounds. Strong acids, for the purposes of the invention, means organic or inorganic acids which are inert under the reaction conditions and have an acid exponent (pKa) of from −7 to +2.16; as regards the definition of the acid exponent or the pKa, reference may be made to Ullmanns Encyklopadie der technischen Chemie, volume 15, page 2. Examples of suitable acids are sulfuric acid, advantageously of from 10 to 98 percent strength by weight, phosphoric acid, advantageously of from 70 to 90 percent strength by weight, hydrochloric acid, advantageously of from 10 to 35 percent strength by weight, nitric acid, advantageously of from 60 to 98 percent strength by weight, perchloric acid, advantageously of from 10 to 70 percent strength by weight and formic acid, advantageously of from 10 to 98 percent strength by weight. It is also possible to use hydrogen chloride gas, boric acid, sulfonic acids, eg. benzenesulfonic acid and p-toluenesulfonic acid, trichloroacetic acid, acidic ion exchangers, such as those described in Houben-Weyl, Methoden der Organischen Chemie, volume I/1, pages 528 et seq., preferably polystyrenesulfonic acid resins, phenolsulfonic acid resins and polyfluoroethylene-sulfonic acids, or mixtures of the above. Preferred acids are concentrated hydrochloric acids or sulfuric acid or phosphoric acid, especially in the above concentrations. The acid is advantageously used in an amount of from 0.01 to 5, preferably from 0.1 to 1, percent by weight, based on the weight of starting material.

In the case of a basic compound, the reaction is advantageously carried out with from 0.01 to 5, preferably from 0.05 to 1, percent by weight of basic compound, based on the weight of starting material. Advantageous basic compounds are tertiary amines, alkaline earth metal compounds, ammonium compounds, tertiary phosphines and alkali metal compounds, as well as mixtures of the above. However, zinc compounds and primary or secondary amines can also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene-glycollate, sodium 1,2-propylene-glycollate, sodium 1,3-propylene-glycollate, sodium diethylene-glycollate, sodium triethylene-glycollate, sodium 1,2-dipropylene-glycollate, potassium methylate, potassium ethylate, potassium n-propylate, potassium isopropylate, potassium n-butylate, potassium isobutylate, potassium sec.-butylate, potassium tert.-butylate, potassium ethylene-glycollate, potassium 1,2-propylene-glycollate, potassium 1,3-propylene-glycollate, potassium diethyleneglycollate, potassium triethylene-glycollate, potassium 1,2-dipropylene-glycollate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N,N-dimethylaminoethanol, N,N-diethylaminoethanol, N,N-dipropylaminoethanol, triisopropanolamine, triethanolamine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine, triethylenediamine, dimethylamine, diethylamine, dipropylamine, diisopropylamine, dibutylamine, diisobutylamine, di-sec.-butylamine, di-tert.-butylamine, dibenzylamine, dicyclohexylamine, diamylamine, dihexylamine, N-methylaniline, N-ethylaniline, N-propylaniline, N-methyltoluidine, N-ethyltoluidine, N-propyltoluidine, N-methylaminoethanol, N-ethylaminoethanol, N-propylaminoethanol, pyrrolidone, piperidine, pyrrolidine, imidazole, pyrrole, N,N'-dimethylethylenediamine, N,N'-diethylethylenediamine, morpholine, hexamethyleneimine, difurfurylamine, N-methylcyclohexylamine, methylamine, ethylamine, propylamine, isopropylamine, butylamine, sec.-butylamine, tert.-butylamine, benzylamine, hexylamine, cyclohexylamine, amylamine, aniline, toluidine, aminoethanol, ethylenediamine, furfurylamine, ammonium acetate, ammonium propionate, tetrabutylammonium hydroxide, trimethylbenzylammonium hydroxide, triethyl-phosphine, tri-n-propyl-phosphine, triisopropylphosphine, tri-n-butyl-phosphine, triphenyl-phosphine, tri-(2-cyanoethyl)-phosphine, bis-(2-cyanoethyl)-phenyl-phosphine and bis-(ethyl)-phenyl-phosphine.

It is particularly advantageous to use phosphoric acid and, preferably, tertiary amines, especially the above tertiary amines.

The reaction may be carried out as follows: a mixture of the starting material and the catalyst, with or without solvent, is kept for from 10 seconds to 300 minutes at the reaction temperature. The end product is isolated from the reaction mixture in the conventional manner, as a rule by fractional distillation.

The 3-methyl-2-buten-1-al obtainable by the process of the invention is a valuable starting material for the preparation of dyes, pesticides, drugs, plastics, naturally occuring materials and scents, eg. citral, vitamins, eg. vitamins A and E, chrysanthemic acid and β-ionone. Regarding their use, reference may be made to German Patent No. 2,243,810, German Laid-Open Application No. DOS 2,041,976, German Patent No. 2,020,865 and U.S. Pat. No. 2,042,220. Hitherto, it has only been possible to prepare α,β-unsaturated aldehydes unsatisfactorily, in respect of yield, purity of the end product and simplicity and economy of operation, from α,β- or β,γ-unsaturated alcohols. The preparation of 3-alkyl-2-buten-1-ols, especially of 3-methyl-2-buten-1-ol, is expensive; on the other hand the corresponding 3-butene compounds are more easily accessible; for example 3-methyl-3-buten-1-ol may be obtained from isobutene and formaldehyde. Accordingly, the oxidation of 3-methyl-3-buten-1-ol to give 3-methyl-3-buten-1-al, and the subsequent isomerization of the reaction mixture, provides a simple and economical method of preparing 3-methyl-2-buten-1-al, an intermediate for the synthesis of citral, in better yield and greater purity.

In the Examples which follow, parts are by weight.

EXAMPLE 1

0.4 part of 75 percent strength aqueous phosphoric acid is added to 69.2 parts of 3-methyl-3-buten-1-al and the mixture is heated in a pressure vessel to 140° C. in the course of 5 minutes, whilst bringing the total pressure to 10 bars with nitrogen. After 70 minutes at the above temperature, the mixture is cooled to room temperature in the course of 5 minutes. After neutralizing the phosphoric acid, distillation at 100 mm Hg gives 4.2 parts of uncoverted 3-methyl-3-buten-1-al and 61.8 parts (95% of theory) of 3-methyl-2-buten-1-al of boiling point 77° C. This corresponds to a conversion of 94 percent.

EXAMPLE 2

0.16 part of triethylamine is added to 81.2 parts of 3-methyl-3-buten-1-al and the mixture is heated in a pressure vessel to 170° C., at 10 bars pressure, in the course of 8 minutes. Immediately after reaching the set temperature, the mixture is again cooled to 50° C. in the course of 5 minutes. Distillation at 100 mm Hg gives 1.6 parts of unconverted 3-methyl-3-buten-1-al and 78.0 parts (98% of theory) of 3-methyl-2-buten-1-al of boiling point 77° C. This corresponds to a conversion of 98 percent.

EXAMPLE 3

0.5 part of tri-n-butylamine is added to 97 parts of 3-methyl-3-buten-1-al and the mixture is heated for 30 minutes at 75° C. at 1 bar pressure. It is then distilled for 10 minutes at 20 mm Hg to separate the mixture from the catalyst; the distillate thus obtained is then fractionally distilled at 100 mm Hg to give 3 parts of unconverted 3-methyl-3-buten-1-al and 93 parts (99% of theory) of 3-methyl-2-buten-1-al of boiling point 77° C. This corresponds to a conversion of 97 percent.

EXAMPLE 4

Per hour, 2 parts of tri-n-butylamine are added to 1,000 parts of 3-methyl-3-buten-1-al and the mixture is passed for 2 minutes through a reaction tube at 220° C. and 12 bars. Distillation at 100 mm Hg gives 20 parts per hour of unconverted 3-methyl-3-buten-1-al and 970 parts per hour (99% of theory) of 3-methyl-2-buten-1-al of boiling point 77° C. This corresponds to a conversion of 98 percent.

We claim:

1. A process for the preparation of 3-methyl-2-buten-1-al which comprises isomerizing the unsaturated compound 3-methyl-3-buten-1-al at from 50° to 250° C. in the presence of an isomerization catalyst selected from the group consisting of strong acids having acid exponents (pKa) of from −7 to +2.16, and tertiary amines, alkaline earth metal compounds, alkali metal compounds, ammonium compounds and tertiary phosphines as basic compounds.

2. A process as claimed in claim 1, wherein the isomerization is carried out at from 72° to 225° C.

3. A process as claimed in claim 1, wherein the isomerization is carried out at from 120° to 225° C.

4. A process as claimed in claim 1, wherein the isomerization is carried out with residence times of from 10 seconds to 300 minutes.

5. A process as claimed in claim 1, wherein the isomerization is carried out with water in an amount of from 0 to 50 percent by weight, based on the starting material.

6. A process as claimed in claim 1, wherein the isomerization is carried out with an organic solvent in an amount of from 0 to 50 percent by weight, based on the starting material.

7. A process as claimed in claim 1, wherein the isomerization is carried out with from 0.01 to 5 percent by weight of acid as the isomerization catalyst, based on the weight of starting material.

8. A process as claimed in claim 1, wherein the isomerization is carried out with from 0.01 to 5 percent by weight of basic compound as the isomerization catalyst, based on the weight of starting material.

9. A process as claimed in claim 7 wherein said acid is selected from the group consisting of sulfuric acid, phosphoric acid, hydrochloric acid, nitric acid, perchloric acid, formic acid, hydrogen chloride gas, boric acid, benzenesulfonic acid, p-toluenesulfonic acid, trichloroacetic acid, polystyrenesulfonic acid resins, phenolsulfonic acid resins and polyfluoroethylenesulfonic acids.

10. A process as claimed in claim 8 wherein said basic compound is selected from the group consisting of potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, sodium propionate, sodium butyrate, sodium isobutyrate, potassium formate, potassium acetate, potassium propionate, potassium butyrate, potassium isobutyrate sodium methylate, sodium ethylate sodium propylate, sodium isopropylate, sodium butylate, sodium isobutylate, sodium sec.-butylate, sodium tert.-butylate, sodium ethylene-glycollate, sodium 1,2-propylene-glycollate, sodium 1,3-propylene-glycollate, sodium diethylene-glycollate, sodium triethylene-glycollate, sodium 1,2-dipropylene-glycollate, potassium methylate, potassium ethylate, potassium n-propylate, potassium isopropylate, potassium n-butylate, potassium isobutylate, potassium sec.-butylate, potassium tert.-butylate, potassium ethylene-glycollate, potassium 1,2-propylene-glycollate, potassium 1,3-propylene-glycollate, potassium diethylene-glycollate, potassium triethylene-glycollate, potassium 1,2-dipropylene-glycollate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N,N-dimethylaminoethanol, N,N-diethylaminoethanol, N,N-dipropylaminoethanol, triisopropanolamine, triethanolamine, N-methylpyrrolidone, N-ethylpyrrolidone, N-methylpiperidine, N-ethylpiperidine, N-methylpyrrolidone, N-ethylpyrrolidone, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine, triethylenediamine, dimethylamine, diethylamine, dipropylamine, diisopropylamine, dibutylamine, diisobutylamine, di-sec.-butylamine, di-tert.-butylamine, dibenzylamine, dicyclohexylamine, diamylamine, dihexylamine, N-methylaniline, N-ethylaniline, N-propylaniline, N-methyltoluidine, N-ethyltoluidine, N-propyltoluidine, N-methylaminoethanol, N-ethylaminoethanol, N-propylaminoethanol, pyrrolidone, piperidine, pyrrolidine, imidazole, pyrrole, N,N'-dimethylethylenediamine, N,N'-diethylethylenediamine, morpholine, hexamethyleneimine, difurfurylamine, N-methylcyclohexylamine, methylamine, ethylamine, propylamine, isopropylamine, butylamine, sec.-butylamine, tert.-butylamine, benzylamine, hexylamine, cyclohexylamine, amylamine, aniline, toluidine, aminoethanol, ethylenediamine, furfurylamine, ammonium acetate, ammonium propionate, tetrabutylammonium hydroxide, trimethylbenzylammonium hydroxide, triethyl-phosphine, tri-n-propyl-phosphine, triisopropylphosphine, tri-n-butyl-phosphine, triphenyl-phosphine, tri-(2-cyanoethyl)-phosphine, bis-(2-cyanoethyl)-phenyl-phosphine and bis-(ethyl)-phenyl-phosphine.

* * * * *